United States Patent
Blum et al.

(10) Patent No.: US 11,961,599 B2
(45) Date of Patent: Apr. 16, 2024

(54) METHOD FOR AUTHORIZING AND ACCESSING MEDICATION PARAMETERS FOR PRESCRIPTION MEDICATIONS

(71) Applicant: Alto Pharmacy LLC, San Francisco, CA (US)

(72) Inventors: Matthew Blum, San Francisco, CA (US); Matthew Crowley, San Francisco, CA (US); Lauren Meleney, San Francisco, CA (US)

(73) Assignee: Alto Pharmacy LLC, San Francisco, CA (US)

( * ) Notice: Subject to any disclaimer, the term of this patent is extended or adjusted under 35 U.S.C. 154(b) by 1192 days.

(21) Appl. No.: 15/353,318

(22) Filed: Nov. 16, 2016

(65) Prior Publication Data

US 2017/0193191 A1 Jul. 6, 2017

Related U.S. Application Data (60) Provisional application No. 62/255,917, filed on Nov. 16, 2015.

(51) Int. Cl.
*G16H 20/13* (2018.01)

(52) U.S. Cl.
CPC .................. *G16H 20/13* (2018.01)

(58) Field of Classification Search
CPC ........ G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00; G06F 19/3462; G06Q 50/22–24

(Continued)

(56) References Cited

U.S. PATENT DOCUMENTS 5,392,952 A * 2/1995 Bowden ................ A61J 7/0481
221/15
6,439,422 B1 * 8/2002 Papp .................. B65D 83/0454
221/13

(Continued)

OTHER PUBLICATIONS

H. Yeh, P. Hsiu, C. Shih, P. Tsai and J. W. S. Liu, "APAMAT: A Prescription Algebra for Medication Authoring Tool," 2006 IEEE International Conference on Systems, Man and Cybernetics, Taipei, 2006, pp. 4284-4291, doi: 10.1109/ICSMC.2006.384807.*

(Continued)

*Primary Examiner* — Robert W Morgan
*Assistant Examiner* — Charles P Coleman
(74) *Attorney, Agent, or Firm* — Sheppard Mullin Richter & Hampton LLP (57) ABSTRACT

One variation of a method for accessing medication parameters for prescription medications includes: reading a unique identifier from a medication cartridge installed in a medication dispenser; based on the unique identifier and a dispenser identifier assigned to the medication dispenser, confirming assignment of the medication cartridge to the medication dispenser; based on the dispenser identifier, retrieving medication parameters for a medication contained in the medication cartridge; and at the medication dispenser, outputting a dynamic visual queue to consume a dose of the medication from the medication cartridge during a medication window, the medication window of a duration based on the medication parameters.

23 Claims, 5 Drawing Sheets

(58) Field of Classification Search
USPC ................................................. 705/2, 3, 20
See application file for complete search history.

(56) References Cited

U.S. PATENT DOCUMENTS

| | | | | |
|---|---|---|---|---|
| 2003/0127463 A1* | 7/2003 | Varis | ........................ | G07F 11/62 221/2 |
| 2003/0200726 A1* | 10/2003 | Rast | .................... | G06F 19/3418 53/443 |
| 2004/0094564 A1* | 5/2004 | Papp | ...................... | A61J 7/0084 221/25 |
| 2004/0172163 A1* | 9/2004 | Varis | ........................ | G07F 11/50 700/237 |
| 2005/0240305 A1* | 10/2005 | Bogash | ............... | G06F 19/3462 700/242 |
| 2007/0185615 A1* | 8/2007 | Bossi | .................. | G07F 17/0092 700/244 |
| 2008/0059228 A1* | 3/2008 | Bossi | .................. | G06F 19/3418 705/2 |
| 2010/0268157 A1* | 10/2010 | Wehba | .................... | G16H 40/20 604/66 |
| 2013/0088328 A1* | 4/2013 | DiMartino | ............ | A61J 7/0076 340/5.82 |
| 2013/0197693 A1* | 8/2013 | Kamen | .................... | G06F 21/32 700/244 |
| 2014/0114472 A1* | 4/2014 | Bossi | ..................... | A61J 7/0084 700/240 |
| 2014/0277702 A1* | 9/2014 | Shaw | .................... | A61J 7/0481 700/232 |
| 2014/0278510 A1* | 9/2014 | McLean | ................ | A61J 7/0076 705/2 |
| 2015/0039124 A1* | 2/2015 | Mistovich | ............. | A61J 7/0076 700/237 |
| 2015/0051730 A1* | 2/2015 | Portney | ................... | H04W 4/70 700/242 |
| 2016/0162660 A1* | 6/2016 | Strong | .................. | A61J 7/0084 221/25 |
| 2016/0203292 A1* | 7/2016 | Kamen | ............... | G06F 19/3462 700/237 |
| 2016/0371462 A1* | 12/2016 | Wallen | ................ | G06F 19/3462 |
| 2017/0011202 A1* | 1/2017 | Kamen | ................ | H04N 5/2257 |
| 2017/0193191 A1* | 7/2017 | Blum | .................. | G06F 19/3462 700/242 |
| 2017/0326033 A1* | 11/2017 | Kraft | ..................... | A61J 7/0418 |
| 2018/0204635 A1* | 7/2018 | McLean | ................ | A61J 7/0076 |
| 2019/0051084 A1* | 2/2019 | Ghouri | .................... | G07F 9/002 |

OTHER PUBLICATIONS

P. h. Tsai, H. c. Yeh, C. y. Yu, P. c. Hsiu, C. s. Shih and J. w. s. Liu, "Compliance Enforcement of Temporal and Dosage Constraints," 2006 27th IEEE International Real-Time Systems Symposium (RTSS'06), Rio de Janeiro, 2006, pp. 359-368, doi: 10.1109/RTSS.2006.14.*

P. H. Tsai et al., "iMAT: Intelligent medication administration tools," The 12th IEEE International Conference on e-Health Networking, Applications and Services, Lyon, 2010, pp. 308-315, doi: 10.1109/HEALTH.2010.5556551.*

Ross, Stephen E et al. "Two complementary personal medication management applications developed on a common platform: case report." Journal of medical Internet research vol. 13,3 e45. Jul. 12, 2011, doi:10.2196/jmir.1815.*

* cited by examiner

METHOD FOR AUTHORIZING AND ACCESSING MEDICATION PARAMETERS FOR PRESCRIPTION MEDICATIONS

CROSS-REFERENCE TO RELATED APPLICATIONS

This Application claims the benefit of U.S. Provisional Application No. 62/255,917, filed on 16 Nov. 2015, which is incorporated in its entirety by this reference.

TECHNICAL FIELD

This invention relates generally to the field of medication dispensers and more specifically to a new and useful method for accessing medication parameters for prescription medications in the field of medication dispensers.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method and Variations

Figure 1:
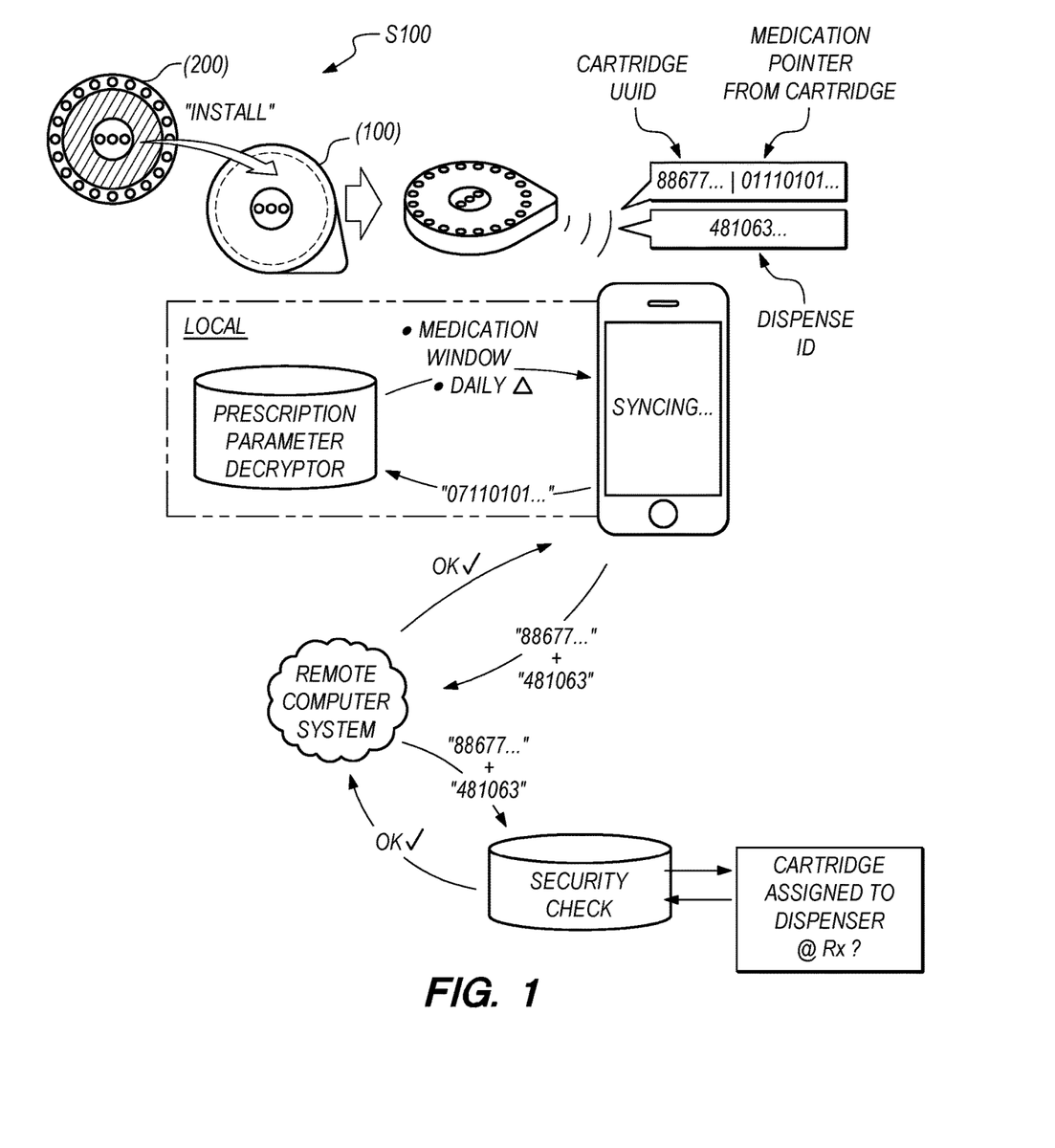
FIG. 1 is a flowchart representation of a method.

As shown in FIG. 1, a first variation of a method S100 for accessing medication parameters for prescription medications includes: reading a unique identifier from a medication cartridge installed in a medication dispenser; based on the unique identifier and a dispenser identifier assigned to the medication dispenser, confirming assignment of the medication cartridge to the medication dispenser; based on the dispenser identifier, retrieving medication parameters for a medication contained in the medication cartridge; and at the medication dispenser, outputting a dynamic visual queue to consume a dose of the medication from the medication cartridge during a medication window, the medication window of a duration based on the medication parameters.

Figure 2:
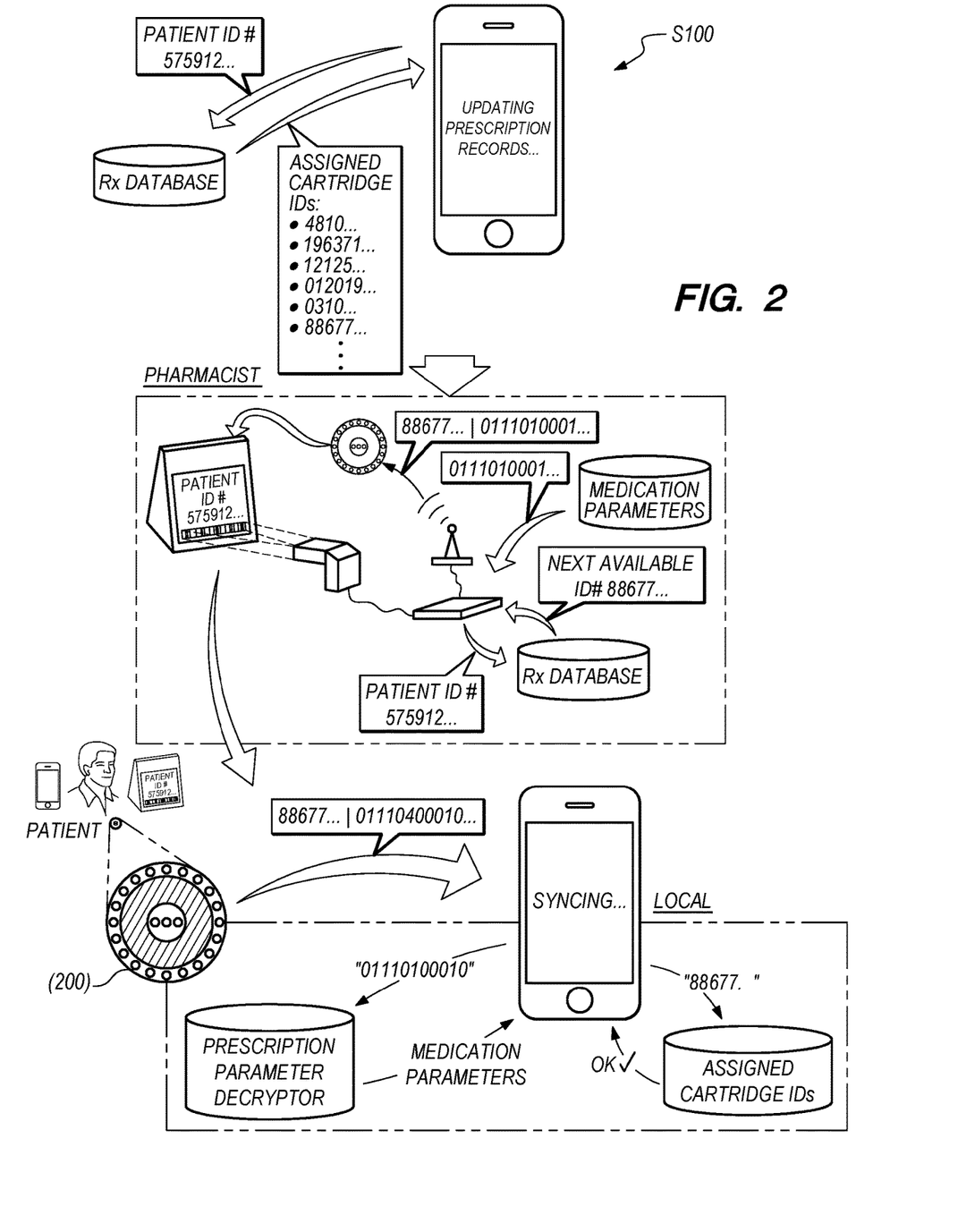
FIG. 2 is a flowchart representation of one variation of the method.

As shown in FIG. 2, a second variation of the method S100 includes: reading a unique identifier from a medication cartridge installed in a medication dispenser; based on a first segment of the unique identifier and a dispenser identifier assigned to the medication dispenser, confirming assignment of the medication cartridge to the medication dispenser; translating a second portion of the dispenser identifier into medication parameters for a medication contained in the medication cartridge; and at the medication dispenser, outputting a dynamic visual queue to consume a dose of the medication from the medication cartridge during a medication window, the medication window of a duration based on the medication parameters.

Figure 3:
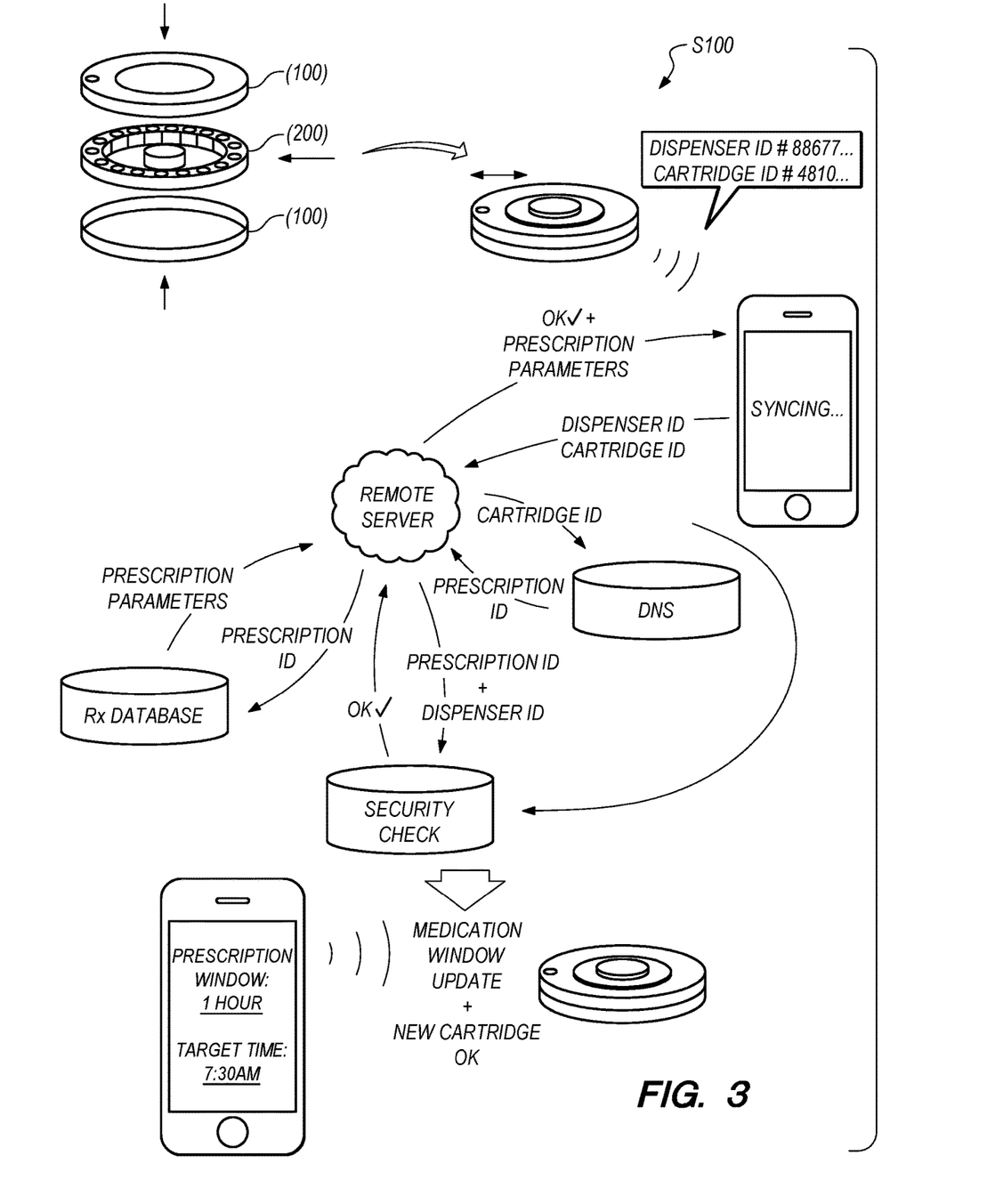
FIG. 3 is a flowchart representation of one variation of the method.
Figure 4:
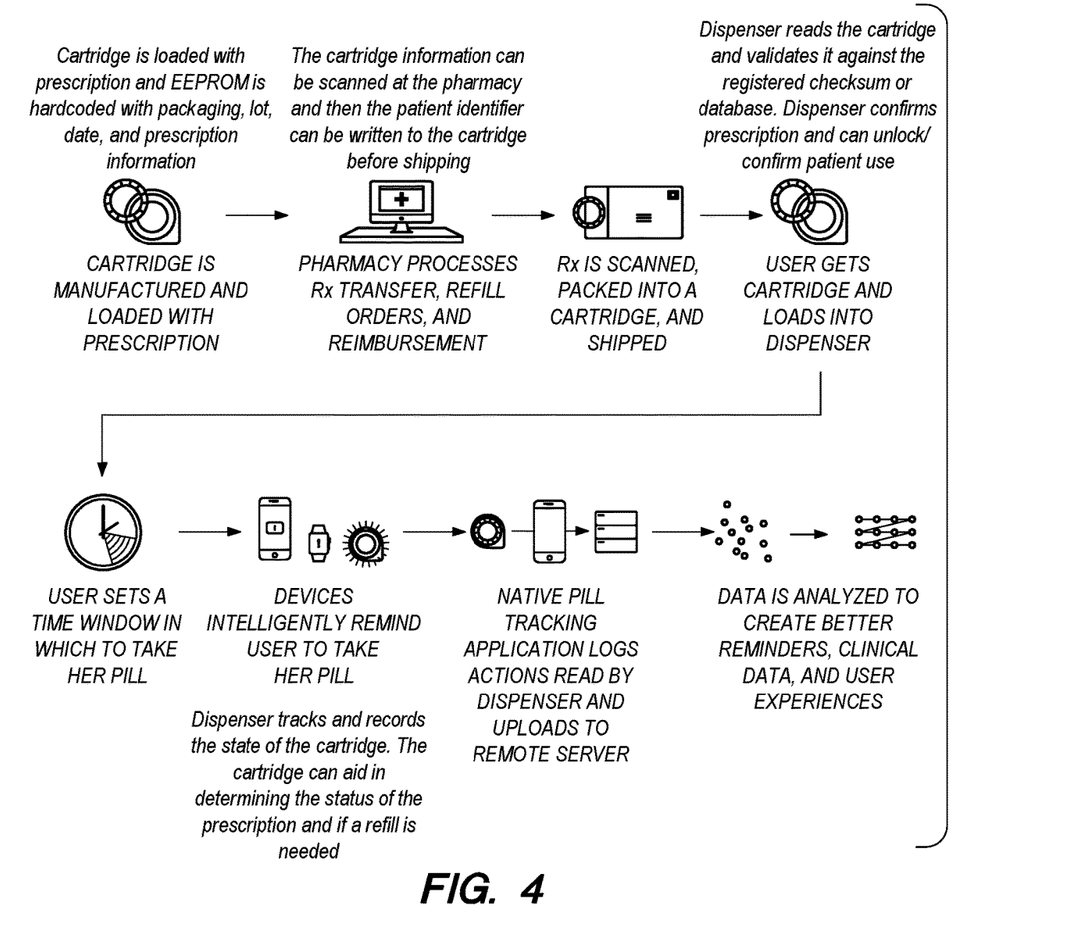
FIG. 4 is a flowchart representation of one variation of the method.

As shown in FIG. 3, a third variation of the method S100 includes: at a first time, downloading a set of medication cartridge identifiers assigned to the a medication dispenser; at a second time succeeding the first time, reading a unique identifier from a medication cartridge installed in a medication dispenser; confirming assignment of the medication cartridge to the medication dispenser based on a match between the unique identifier and a particular medication cartridge identifier in the set of medication cartridge identifiers; reading medication parameters for a medication contained in the medication cartridge from the medication cartridge; and at the medication dispenser, outputting a dynamic visual queue to consume a dose of the medication from the medication cartridge during a medication window, the medication window of a duration based on the medication parameters.

A fourth variation of the method S100 includes: reading a unique identifier from a medication cartridge installed in a medication dispenser; translating the unique identifier into a confirmation code and a medication parameter based on a decrypting scheme stored on the medication dispenser; at the medication dispenser, outputting a dynamic visual queue to consume a dose of the medication from the medication cartridge during a medication window, the medication window of a duration based on the medication parameter.

2. Applications

Generally, Blocks of the method can be executed by a medication dispenser, a native medication tracking application executing on a local computing device (e.g., a smartphone, a tablet), and/or a remote computer system to identify a medication cartridge loaded into the medication dispenser, to confirm that the medication cartridge was assigned or issued to the medication dispenser (or more generally to the corresponding patient), to access medication parameters (e.g., dosage, medication window duration, limits of daily variations in time of medication consumption) for the medication, and to implement the medication parameters when issuing visual and/or audible prompts to the patient to consume medication contained in the medication cartridge. In particular, the medication dispenser, the native medication tracking application, and/or the remote server can—independently or in cooperation—implement Blocks of the method: to selectively enable medication adherence tracking and medication consumption prompts based on confirmation of assignment of a medication cartridge to the patient; and to automatically retrieve and implement medication parameters specific to the medication cartridge.

In the first variation of the method, a unique identifier (e.g., a universally unique ID, hereafter a "UUID") is loaded onto a medication cartridge sans personal patient data, direct identification of the medication contained in the medication cartridge, or medication parameters for the medication. For example, in this variation, when the pharmacy fulfills a prescription for a patient, the pharmacy can read the unique identifier from the medication cartridge and link the unique identifier to the patient, such as to an identifier stored on a medication dispenser assigned to the patient. In this example, the pharmacy can also link the unique identifier with custom medication parameters for the patient, such as by overwriting general medication parameters associated with the unique identifier by a medication packaging facility that previously processed the medication cartridge. The unique identifier of the medication cartridge, the dispenser identifier, and a pointer to medication parameters for the medication contained in the medication cartridge can be stored in a remote name mapping system (or "NMS," e.g., a DNS) server, and the medication parameters can be similarly stored in a remote prescription database. Subsequently, upon receipt of the medication cartridge from the pharmacy, the patient can install the medication cartridge into her (or his) medication dispenser. The medication dispenser reads the unique identifier from the medication cartridge and uploads the unique identifier and its assigned dispenser identifier to a local mobile computing device (e.g., the patient's smartphone) paired with the medication dispenser. The local mobile computing device uploads the unique identifier and dispenser identifier to the remote NMS server and remote prescription database, which return confirmation of assignment of the medication cartridge to the patient and corresponding medication parameters, respectively. In this variation, the medication cartridge and medication dispenser can thus exclude both patient data and medication data, and a remote NMS and remote prescription database can upload medication parameters—such as daily dosage, duration of a medication consumption window, limit of day-to-day variation in medication consumption time, sans data identifying the medication—to the mobile computing device, which can adjust medication consumption windows implemented between the mobile computing device and the medication dispenser accordingly.

In the second variation of the method, both a unique identifier and medication parameters are loaded onto the cartridge sans personal patient data or direct identification of the medication contained in the medication cartridge. For example, in this variation, when the pharmacy fulfills a prescription for the patient, the pharmacy can generate a 32-bit unique identifier, encode custom or generic medication parameters for the medication into a 32-bit string, and write a contiguous 64-bit string including the unique identifier and the encoded medication parameters to the medication dispenser. As in the first variation, the pharmacy can also link the unique identifier to the patient, such by associating the unique identifier with the dispenser identifier—stored on the patient's medication dispenser—in the remote NMS. Subsequently, upon receipt of the medication cartridge from the pharmacy, the patient can install the medication cartridge into her (or his) medication dispenser. The medication dispenser can then read the 64-bit string from the medication cartridge and upload the 64-bit string and its assigned dispenser identifier to the patient's mobile computing device. The local mobile computing device can separate the unique identifier from the encoded medication parameters in the 64-bit string and then pass the unique identifier and the dispenser identifier to the remote NMS, which can return confirmation of assignment of the medication cartridge to the patient. Once confirmation for the medication is received, the mobile computing device can decode the 32-bit medication string into medication parameters for the medication now loaded into the medication dispenser, and the mobile computing device and/or the medication dispenser can implement these medication parameters until the medication cartridge is removed from the medication dispenser. Therefore, in the second variation of the method, the medication cartridge can store medication parameters directly such that the mobile computing device and/or the medication dispenser can access and implement daily dosage, medication consumption window duration, day-to-day medication consumption variability limits, and/or other medication parameters for the medication contained in the medication cartridge regardless of connectivity (e.g., Internet connectivity). However, in the second variation, the medication cartridge and medication dispenser can exclude patient identification data, and the mobile computing device can receive confirmation from a remote computer system (e.g., the NMS) that stores a link between the medication cartridge and the medication dispenser.

In the third variation of the method, the pharmacy associates a patient ID and/or a dispenser ID with a set of cartridge IDs that span a duration of the prescription in which multiple sequential cartridges will be consumed by the patient and stores these cartridge IDs in a digital medication record for the patient, such as in a remote database or in the remote NMS server. For example, the pharmacy can assign 12 cartridge IDs to a patient for 12 months of a prescription contraceptive medication. When preparing to fulfill a first cartridge in the prescription, the pharmacy can retrieve the cartridge IDs previously assigned to the patient in the patient's digital medication record, select a first available cartridge ID from this list, and write the selected cartridge ID to the cartridge, such as with medication parameters for the prescription as in the second variation described above. Once the first cartridge is supplied to the patient and installed in the patient's medication dispenser, the medication dispenser can read the first cartridge ID to the patient's mobile computing device, and the patient's mobile computing device can upload the first cartridge ID and a patient identifier (e.g., a dispenser ID, a mobile computing device ID) to the remote computer system. The remote computer system can then access the patient's digital medication record based on the patient identifier, authenticate the first cartridge ID for use in the medication dispenser by matching the first cartridge ID to the patient's digital medication record, and then uploads the list of cartridge IDs assigned to the patient and medication parameters for the prescription set to the patient's mobile computing device or the medication dispenser via the patient's mobile computing device. Alternatively, the remote computer system can queue the set of cartridge IDs assigned to the patient for delivery to the patient's mobile computing device, and the remote computer system can upload the cartridge IDs to the mobile computing device when the mobile computing device connects to the Internet. When fulfilling a second cartridge in the prescription for the patient, the pharmacy can assign a next available cartridge ID—in the set of preauthorized IDs for the prescription—to the second cartridge, remove this assigned cartridge ID from an assignable pool of IDs for the patient, and then ship the second cartridge to the patient. The patient's medication dispenser and/or mobile computing device can thus authenticate use of the second cartridge—and subsequent cartridges—with the medication dispenser without an Internet connection because the local computing device and/or medication dispenser now store all (or a significant duration of) valid cartridge IDs for the prescription and can authenticate cartridges locally.

In the fourth variation of the method, before shipping a medication cartridge to a patient, the pharmacy encodes the medication cartridge with an encrypted 64-bit string for which a decryption scheme is stored locally on the patient's medication dispenser and/or the patient's mobile computing device. For example, once decrypted, the cartridge ID can point to corresponding information for the medication contained in the cartridge, such as medication parameters and patient data, or the decrypted cartridge ID can contain this information directly. In this example, when a cartridge is installed in the medication dispenser, the medication dispenser can read the encrypted ID from the cartridge, and the medication dispenser and/or the patient's local computing device can decrypt the encrypted cartridge ID with a 64-bit key stored locally and can then authorize use of the cartridge in the medication dispenser accordingly. The patient's mobile computing device (specifically, the native medication tracking application executing on the patient's mobile computing device) can then extract medication parameters for the cartridge from the decrypted ID and implement these medication parameters to set medication windows and to deliver medication-related notifications to the patient. In this variation, the native medication tracking application and the medication dispenser can thus authorize use of the cartridge in the medication dispenser without local Internet connectivity while still masking personal and prescription information from unauthorized access.

3. Medication Cartridge

Figure 5A:
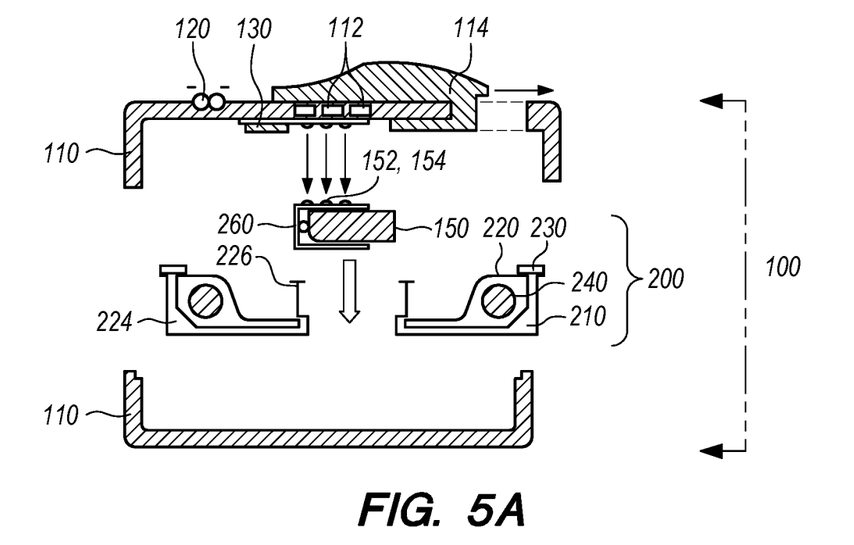
FIGS. 5A and 5B are schematic representations of a medication dispenser and medication cartridge.
Figure 5B:
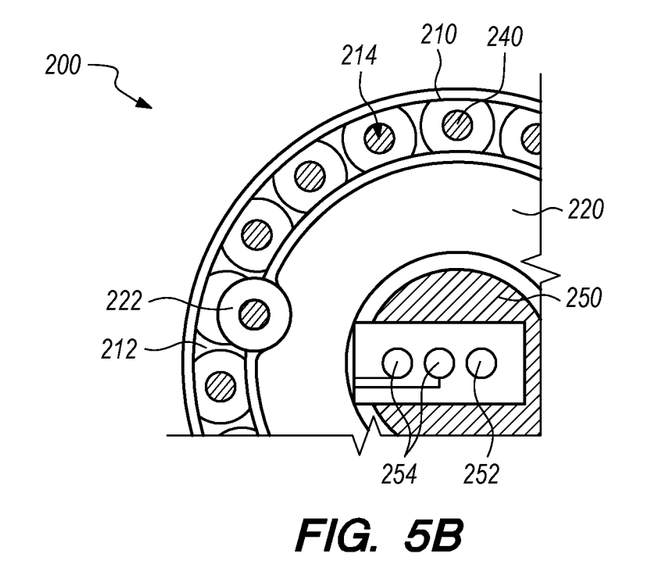

As shown in FIGS. 5A and 5B, Blocks of the method can be executed by or in conjunction with a medication dispenser 100 and a medication cartridge 200. Generally, the medication cartridge 200 functions to (physically) store one or more discrete medication doses in pill form and to (digitally) store identification data for the medication cartridge 200, such as in the form of a UUID.

In one implementation, the medication cartridge 200 defines a radial blister including a tray 210, a cover 220, and a seal 230, as shown in FIGS. 5A and 5B. The tray can include a circular base, a cylindrical wall extending from the perimeter of the circular base, and 29 ribs 212 extending from the corner between the circular base and the cylindrical wall. The 29 ribs are arranged about a common center, are radially offset by a common radial distance (e.g., ~12.4°), and extend from the cylindrical wall toward the common center by a distance slightly greater than (e.g., 20% greater than) the greatest dimension of a pill 240 designated for the medication cartridge 200. The 29 ribs, circular base, and cylindrical wall cooperate to define 29 wells 214; each of 28 of the 29 wells can loaded with a (single) pill, and the $29^{th}$ well can define an empty "start" position. The cover defines an annular ring configured to enclose the ribs when installed over the tray. The cover defines a single orifice 222 configured to align with a single well in the tray, and the tray is configured to rotate relative to the cover to sequentially expose each well to the orifice; a pill contained in a well in the medication cartridge 200 can thus be released from the medication cartridge 200 from aligning the orifice in the cover with the corresponding well in the tray.

In the foregoing implementation, the perimeter region of the circular base can be declined toward the center of the circular base such that the base of each well defines a ramp 224; when the medication cartridge 200 is held upright, a well in the medication cartridge 200 can thus guide its corresponding pill toward the center of the circular base. The cover can also define a bulge aligned with the orifice and extending toward the axial center of the cover (e.g., by a distance less than a greatest dimension of pills stored in the medication cartridge 200). Thus, when the orifice is aligned with a well containing a pill, the ramped bottom of the well can guide the pill into the bulge in the cover such that the pill wedges between the bulge and the adjacent walls of the well, thereby preventing the tray from rotating relative to the cover until the pill is removed from the well via the adjacent orifice in the cover.

In the foregoing implementation, the medication cartridge 200 also includes a seal configured to seal a junction between the tray and the cover and to enclose the orifice in the cover. For example, the tray and cover can define translucent (e.g., substantially transparent) polymer structures, and the seal can include a paper- or polymer-backed aluminum foil sheath bonded to both the tray and to the cover and across a junction between the tray and the cover. The seal can thus cooperate with the tray and cover to maintain an isolated environment within the medication cartridge 200 and to protect pills contained within the medication cartridge 200 from dust, dirt, changes in ambient humidity, and UV/light exposure.

The medication cartridge 200 can be supplied to the patient with the orifice aligned with the $29^{th}$ "start" well and with the seal in place over the tray and cover. To install the medication cartridge 200 into the medication dispenser 100, the patient removes and discards the seal, opens the dispenser, inserts the medication cartridge 200 into the dispenser, and closes the dispenser. As described below, the patient can then actuate the medication dispenser 10o to reveal the orifice in order to remove a pill from an adjacent well. The tray can also include an array of teeth, such as one tooth per well; the array of teeth can be configured to engage a ratchet mechanism within the medication dispenser 100 such that actuation of the medication dispenser 100 actuates the ratchet mechanism, which indexes the tray to a next position relative to cover and thereby exposes a next pill to the orifice (or vice versa). Alternatively, the cartridge can be indexed manually within the medication dispenser 100, such as with a thumbwheel extending from the cover and accessible through a window on a side of the medication dispenser 100. The medication dispenser 100 can also include a ratchet or one-way bearing that retracts rotation of the medication cartridge 200 to a single direction within the medication dispenser 100.

The medication cartridge 200 can also include a battery 250, a ground terminal 252, and a power terminal 254. For example, the medication cartridge 200 can include a coin-cell battery aligned axially with and mounted to the cover, and the ground and power terminals can be arranged over the battery opposite the cover. In particular, the battery can include a lead that extends from the bottom of the battery to the top of the battery to form the ground terminal and a via on the top of the battery that define the power terminal. In this example, the cover can define a cylindrical cup extending away from the tray and including a lip 226 extending inwardly toward the axis of the cup; the battery can be snapped into the cup and retained in the cup by the lip. When the medication cartridge 200 is installed in a medication dispense, the battery can thus supply power to the medication dispenser 100, such as to detect medication consumption events, to transmit medication consumption data to the patient's mobile computing device, to receive medication window parameters from the patient's mobile computing device, and/or to issue medication consumption prompts via a visual, audible, haptic, or other mechanism within the medication dispenser 100.

The battery can be sized (e.g., can be characterized by a particular number of amp-hours) according to a prescribed duration of a prescription contained in the medication cartridge 200. For example, for a medication cartridge 200 containing an oral contraceptive prescription including 28 pills designated for consumption over 28 days, the medication cartridge 200 can include a battery of sufficient size to power a sensor system, a visual display, a wireless communication module, and/or other subsystems within the medication device under greatest anticipated load—with a safety factor—over a 28-day period. In this example, once emptied at the end of the 28-day period, the medication cartridge 200 can be discarded, and a second medication cartridge 200 containing a new set of oral contraceptive pills and a fresh, charged battery can be installed in the medication device, thereby eliminating a need to recharge a battery integrated into the medication device, eliminating a need to replace the medication device, and eliminating a need to replace a separate battery—in addition to the medication cartridge 200—in the medication dispenser 100 at any point during its use.

The medication cartridge 200 can also include an integrated circuit configured to store an identifier (e.g., a UUID) assigned to the medication cartridge 200. In one example, the medication cartridge 200 includes: a flexible circuit board extending between the top and bottom of the battery and defining a ground terminal, a power terminal (as described above), and a data terminal across the top of the battery (i.e., opposite the circular base of the medication cartridge 200); and an ID chip 26o configured to store a unique ID, arranged on the flexible circuit board, receiving power from the battery via the ground and power terminals, and configured to output the unique ID via the data terminal, such as when requested by the medication dispenser 100 via I2C communication protocol. In another example, the medication cartridge 200 includes a short-range wireless communication module that broadcasts a unique ID when pairing wirelessly with a wireless communication module within the medication dispenser 100. In yet another example, the medication cartridge 200 includes an RFID tag configured to wirelessly broadcast a unique ID when driven by an RFID reader in the medication dispenser 100. In this implementation, the ID chip (or wireless communication module, RFID tag, etc.) can be preprogrammed with a unique ID: by a chip manufacturer, such as in the first variation of the method; by a medication packaging facility, such as in the second variation of the method; or by the pharmacy fulfilling a prescription for the patient, such as in the third and fourth variations of the method.

4. Medication Dispenser !

The medication dispenser 100: functions to accept medication cartridge 200S and to release discrete medication doses from the medication cartridge 200; includes a visual display 120 (e.g., one or more LEDs, an e-ink display) that issues a visual prompt to indicate to a user when to consume a medication from the medication dispenser 100; includes a sensor system that detects when a pill is removed from the medication dispenser 100; and includes a wireless transmitter 130 that pushes receipt of a pill removal event to an external device, such as to a wireless communication hub (e.g., Wi-Fi router, wireless-enabled thermostat) or to a mobile computing device wirelessly-paired to the medication dispenser 100. The medication dispenser 100 can additionally or alternatively include an audio driver (e.g., a speaker), a haptic feedback driver (e.g., a vibrator), or any other type of interface configured to provide a perceptible reminder or feedback to the user to consume a medication.

The medication dispenser 100 can include a clamshell no or two-part structure defining a cavity configured to receive the medication cartridge 200, as shown in FIG. 5A. In one implementation, the medication dispenser 100 includes: a first dispenser component that defines a cylindrical cavity configured to receive the medication cartridge 200 with the ground, power, and data terminals on the medication cartridge 200 facing outward from the first dispenser component; and a second dispenser component configured to seat over the medication cartridge 200 and including ground, power, and data electrical junction configured to mate with corresponding terminals on the medication cartridge 200 when the medication dispenser 100 is assembled. For example, each ground, power, and data electrical junction in the second dispenser component can be backed by a magnet 112 that draws the battery toward the second dispenser component, thereby ensuring persistent electrical contact between the electrical junction and the corresponding terminal in the medication cartridge 200. The battery in the medication cartridge 200 can therefore serve as both a power source for the medication dispenser 100 and a ferromagnetic substrate to which magnets in the second dispenser component attract in order to maintain the medication dispenser 100 and the medication cartridge 200 in an assembled state. However, the dispenser components can connect and integrate with the cartridge over any other suitable interface, such as a set of pogo pins or a male/female plug/socket interface.

In the foregoing example, the first dispenser component can be configured to constrain the tray of the medication cartridge 200 radially, and the second dispenser component can be similarly configured to constrain the cover of the medication cartridge 200 radially; the patient can thus rotate the first and second dispenser components relative to one another to index wells in the tray into alignment within the orifice in the cover. Alternatively, the second dispenser component can include a lid 114: configured to open and close over the orifice in the cover; and connected to a ratchet mechanism, as described above. The patient can thus draw the lid from the closed position to the open position to reveal the orifice, invert the medication dispenser 100 to release a pill from a well in a dispense position adjacent the orifice, and then push the lid back into the closed position, which in turn advances the ratchet mechanism and indexes the tray in the medication cartridge 200 forward by one well position relative to the orifice, thereby preparing the medication dispenser 100 to expose another pill when the lid is again opened.

In the foregoing example, the second dispenser component can also include: a short-range wireless communication module configured to send medication consumption event data to the patient's mobile computing device and to receive medication window and clock updates from the mobile computing device; a visual, haptic, and/or auditory output mechanism (e.g., an LED, vibrator, and/or buzzer) configured to indicate to the patient that a medication window is pending; and a sensor configured to detect actuation of the lid or release of a pill through the orifice in the medication cartridge 200, etc. Additionally or alternatively, the sensor can include an accelerometer or tilt sensor that can detect inversion of the dispenser—such as immediately following an index event—and correlate this inversion with dispensation of a pill from the cartridge. However, the medication dispenser 10o can define any other form factor configured to receive pills in blister pack or medication cartridge 200 format, in loose format, or in any other format, and the medication dispenser 100 can detect a medication consumption event in any other suitable way.

5. Prescription Fulfillment

In one implementation, medication cartridges are packaged, encoded, and distributed through a medication system including a pill-manufacturing facility, a pill-packaging facility, and a prescription-dispensing pharmacy. At the pill-manufacturing facility, pills are manufactured in bulk, and the bulk pill containers are labeled with lot numbers, such as lot number associated with pill manufacture dates, manufacture locations, and batch numbers. The pill manufacturing facility can label or associate the bulk pill containers with other general information such as a medication type of the pills, generic dosage parameters for the medication type, and pill expiration dates. A lot number can be printed directly onto a label (e.g., a coded numerical sequence) or encoded as a separate ID (e.g., a barcode, a QR code, an RFID tag) applied to a bulk pill container. The bulk pill container can then be shipped to the pill-packaging facility that packages loose pills into medication cartridges, such as described above. The pill-packaging facility can apply a barcode label, a QR code label, an RFID tag, or other digital identifier—including or pointing to corresponding lot, medication type, dosage, and/or other relevant data—to each cartridge. The pill-packaging facility can additionally or alternatively install a programmable ID chip into each medication cartridge. For example, the pill-packaging facility can install an ID chip pre-programmed with a 32-bit UUID into each medication cartridge. In one or more variations of the method, the pill-packaging facility can link the UUID from each medication cartridge with corresponding lot, medication type, dosage, and/or other relevant information from the pill-manufacturing facility data in a NMS server and/or in a prescription database. The pill-packaging facility can also associate its own lot number, packaging date, facility location, and/or other data with UUIDs stored on ID chips loaded into medication cartridges. The pill-packaging facility can alternatively write a UUID and/or any of the foregoing data to a reprogrammable ID chip installed in each cartridge. In another implementation, the ID chip on the cartridge includes 'write once read many' (WORM) memory; the pill-packaging facility can thus write a UUID and/or any of the foregoing data to a write-once/read-many ID chip in each cartridge, and the medication dispenser can read a cartridge ID from an installed cartridge each time the medication is closed after insertion of a new cartridge, whenever the medication cartridge is jostled, or on a regular schedule (e.g., once per day), or according to any other scheme to confirm use of the cartridge in the medication dispenser. The pill-packaging facility can also install a fresh battery—such as in-unit with the ID chip—into each medication cartridge. (Alternatively, the pharmacy can install a WORM ID chip into a cartridge and encode this ID chip locally with any of the foregoing information, such as a lot number, prescription parameters, and a UUID, as described below. The pharmacy can also package loose pills received directly form the medication manufacturing facility directly into medication cartridges, rather than the pill packaging facility.)

The pill-packaging facility can then supply complete medication cartridges—including pills, battery, and ID chip—to the pharmacy. When fulfilling a prescription for a patient, the pharmacy can read a UUID preloaded onto a cartridge and associate this cartridge ID with an identifier of the patient (a "patient ID"), an identifier of a medication dispenser assigned to the patient (a "medication dispenser ID", and/or an identifier of the prescription (e.g., a "prescription ID"), such as by writing links between these identifiers to a NMS server or to a remote prescription database. Alternatively, the pharmacy can write a new cartridge ID to the medication cartridge. For example, before writing a new cartridge ID to the medication cartridge, the pharmacy can read a UUID previously written to the cartridge by the pill-packaging facility, retrieve relevant information from the manufacturing facility and/or from the pill-packaging facility based on this UUID (e.g., manufacturing date, lot number, generic dosage data, etc.), and associate these data with the new UUID written to the cartridge, such as in the remote prescription database. As described above, the pharmacy can associate the new UUID thus written to the ID chip with a patient ID, a medication dispenser ID, a native medication tracking application ID, etc. and store these data in the patient's medication record.

The pharmacy can also add or modify general information associated with a UUID stored on the ID chip, such as by adjusting generic daily dosage, a generic medication consumption window duration, a generic day-to-day consumption time variation limit, etc. stored in the prescription database and linked to the cartridge ID. Alternatively, the pharmacy can overwrite general information for the cartridge, such as by writing new prescription parameter to the prescription database in the first and second variations or by writing new prescription parameters directly onto the ID chip in the third and fourth variations. For example, the pharmacy can customize prescription parameters for the patient to suit to the patient's specific needs and can write this information to the prescription database such that the patient's mobile computing device can retrieve these custom prescription parameters based on the cartridge ID. In this implementation, the pharmacy can include master dispenser encoder that receives cartridges and encodes ID chips (or RFID tags, Bluetooth chips, etc.) in cartridges loaded into the master dispenser encoder with corresponding cartridge IDs. For example, the master dispenser encoder can include a wireless or contact-based ID chip programmer configured to (re)program an ID chip in a cartridge according to a low frequency standard (125 KHz) in which a UUID is written, according to a high-frequency standard (13.56 MHz) in which 1-2 KB of data are written to the ID chip, or according to an ultra-high-frequency standard (860-960 MHz) in which 64 KB of data are written to the ID chip.

The master dispenser encoder can also download operating system updates or a new operating system for the medication dispenser from a remote computer system and can write these data onto the ID chip. The medication dispenser can download these operating system updates or the new operating system from the cartridge when the cartridge is installed therein.

Additionally or alternatively, the pharmacy can generate, print, and apply a machine-readable optical label (e.g., a QR code, a barcode) that contains any of the foregoing data directly or that includes a pointer to these data, and the medication dispenser can include an optical reader that reads this optical label when the cartridge is installed in therein.

Generally, the pharmacy interfaces with a remote prescription database to associate a cartridge ID with the corresponding patient (with a corresponding patient ID), the medication dispenser ID, the instance of the native medication tracking application executing on the user's mobile computing device, and/or the generic or custom prescription parameters for the patient's prescription. If there is an existing patient ID already in the computer system (e.g., the NMS server, the prescription database), then new prescription IDs and cartridge IDs are associated with the patient ID, and a medication dispenser ID can be added as well. If there is not an existing patient ID, the system creates a new record in the appropriate databases (e.g., the NMS server, the prescription database) and associates the corresponding IDs.

In one variation of the method, the remote computer system can pull information from a patient's electronic medical records (e.g., from a hospital or an insurance carrier record), and the remote computer system can interface with one or more third-party computer systems (e.g., a hospital server, an insurance carrier server) via a specialized NMS server to reconcile different patient identification and patient information formats and nomenclatures. The pharmacy can also dynamically adjust a new prescription based on existing information in the patient record. For example, the pharmacy can modify medication parameters (e.g., dosage amount) for the new prescription based on medications currently prescribed to the patient. In another example, the pharmacy can authorize two or more cartridge IDs for concurrent consumption by the patient, and the pharmacy can cooperate with the native mediation tracking application executing on the patient's smartphone to track the status of multiple cartridges across the multiple medication dispensers assigned to the patient and then modify a future prescription regimen for the patient accordingly.

However, the pharmacy can fulfill a medication cartridge for a patient prescription in any other way and according to any other schema. Once the prescription is fulfilled, the pharmacy can then ship the medication cartridge to the patient.

6. Cartridge Confirmation

Once the medication cartridge is received by the patient, the patient can place the medication cartridge into her assigned medication dispenser; once combined, these elements hereinafter form a "medication dispenser assembly."

Generally, the medication dispenser interfaces with the mobile computing device and/or the remote computer system to determine authenticity of the cartridge by verifying the cartridge ID and confirming that the cartridge has been assigned to the patient by the pharmacy. In one implementation, the medication dispenser is assigned and stores locally a unique identifier associated with one or more external IDs—such as a patient ID, a prescription ID, one or more cartridge IDs, etc.—in the prescription database or in the remote NMS server. The medication dispenser, the patient's mobile computing device (e.g., the native mediation tracking application executing on the patient's smartphone wirelessly paired to the medication dispenser), the prescription database, and/or remote NMS server can thus cooperate to collect IDs from the various elements in the "system," to match IDs assigned to the cartridge and the medication dispenser, and to match IDs assigned to the medication dispenser and to the patient's mobile computing device. If the system fails to match IDs at any stage, the medication dispenser assembly and the native mediation tracking application can disable higher-level functions, such as medication window tracking, medication consumption prompts, medication-related push notifications, medication storage sensor tracking, etc.

6.1 Generic UUID

In the first variation of the method, the pharmacy writes a UUID stored on the medication cartridge to the patient's medication record in the remote computer system. The pharmacy can associate the cartridge ID with a prescription ID in the NMS server, and the prescription ID can store prescription parameters for the medication in the prescription database. The patient's medication record can also store the dispenser ID for the medication dispenser assigned to the patient and an ID for a mobile computing device or instance of the native medication tracking application associated with the patient. These databases can interoperate via a security check performed by the remote computer system to confirm the prescription ID and the dispenser ID for the patient ID. In one example, the medication dispenser assembly reads the cartridge ID from the cartridge once installed and transmits the cartridge ID and its own dispenser ID to the patient's mobile computing device running the native medication tracking application. The mobile computing device transmits the cartridge ID, the dispenser ID, and a native medication tracking application ID to the remote computer system. The remote computer system passes the cartridge ID through the NMS server to retrieve a corresponding prescription ID. The remote computer system then compares the prescription ID to the dispenser ID in a security check/ authentication to confirm assignment to the correct patient in the prescription database. Once authenticated, the prescription ID is transmitted to the prescription database to retrieve prescription parameters for the medication, and the remote computer system pushes these parameters to the patient's mobile computing device if the native medication tracking application ID is matched to the patient ID in the patient medication record. The patient's mobile computing device can thus implement and display these prescription parameters, such as a prescription time interval (e.g., 24 hours), a target prescription administration window (e.g., within 20 minutes of 7:30 am), etc.

6.2 Generic UUID and Prescription Parameters

In the second variation of the method, the dispenser, cartridge, native medication tracking application, and remote computer system can function generally as described. However, in this variation, the cartridge ID can contain two distinct sets of information, including: a cartridge UUID; and a prescription ID. The remote computer system transmits the cartridge UUID and dispenser ID, etc. to the remote computer system, and the remote computer system can implement a security check to confirm the IDs are associated with the patient ID. The native medication tracking application can store a prescription decryption scheme and can decrypt the prescription ID locally in medication parameters for the medication stored in the cartridge. Alternatively, the native medication tracking application can include a lookup stored locally on the mobile computing device, and the native medication tracking application can pass the prescription ID received from the medication dispenser through the lookup table to access generic or custom prescription parameters for the medication cartridge. Yet alternatively, the remote computer system can decrypt the prescription ID and then upload these prescription parameters back to the mobile computing device.

6.3 Pre-Assigned and Preloaded UUIDs

In the third variation of the method, the pharmacy associates the patient ID with multiple cartridge IDs in the patient medication record. The patient medication record can push these preauthorized cartridge IDs to the mobile computing device, or the mobile computing device can pull these cartridge IDs from the patient medication record when connected to the Internet; the mobile computing device can thus store the cartridge IDs locally and offline. Similarly, the pharmacy can assign several preauthorized cartridge IDs (e.g., 12 cartridge IDs for each one-month cartridge refill in a 12-months prescription) to the patient, and the medication dispenser can retrieve the cartridges IDs from the cartridge and store these cartridge IDs in local memory (i.e., rather than on the mobile computing device). In this variation, the pharmacy can also encode prescription parameters into each cartridge, such in the form of a prescription ID as described above.

Alternatively, the pharmacy can print or apply a barcode or RFID tag, etc. to the cartridge or to a cartridge packaging and link the barcode or a UUID on the RFID tag to the preauthorized cartridge IDs assigned to the patient. Upon receipt of the cartridge, the patient can scan the barcode or read the RFID tag with her mobile computing device, which then passes a form of the barcode and RFID UUID to the remove server to retrieve the set of preauthorized cartridge IDs for the patient. However, the cartridge, the medication dispenser, the native medication tracking application executing on the patient's mobile computing device, and/or the remote computer system can cooperate in any other way to access preauthorized cartridge IDs for the patient.

In this variation, when the patient's current cartridge is nearing empty, the patient's mobile computing device can transmit a "near empty" status and the cartridge ID, dispenser ID, device ID, and/or patient ID to the pharmacy (e.g., to the remote computer system), and the pharmacist can write a second cartridge ID—from the set of preauthorized cartridge IDs associated with the patient ID in the prescription database—to a second cartridge for the patient's prescription. For example, the remote computer system can remove the second cartridge ID from the pool of available cartridge IDs and add it to the pool of used cartridge IDs, and the pharmacy can encode the second cartridge with the second cartridge ID and then send (e.g., mail) the second cartridge to the patient. The patient then loads the second cartridge into the medication dispenser, and the dispenser assembly reads the second cartridge ID and prescription ID from the cartridge, authenticates the second cartridge locally based on the second cartridge ID and a pool of cartridge IDs stored locally on the medication dispenser, and transmits the prescription ID to the mobile computing device; the mobile computing device then transforms the prescription ID into a set of prescription parameters, as described above. Alternatively, the dispenser can upload the second cartridge ID and the prescription ID to the mobile computing device directly, and the native medication tracking application can authenticate the second cartridge ID against the stored pool of cartridge IDs to verify use of the second cartridge in the medication dispenser. The mobile computing device and/or the medication dispenser assembly can then implement the prescription parameters to provide medication consumption guidance to the patient and to track medication consumption by the patient.

6.4 Encrypted Confirmation and Medication Parameters

In the fourth variation of the method, when fulfilling a prescription for a patient, the pharmacy writes an encrypted cartridge ID to a medication cartridge according to a known decryptogram stored on the medication dispenser and/or in a native medication tracking application associated with the patient. For example the pharmacy can implement hashing, data compression, symmetric-key cryptography, and/or public-key cryptography techniques—that mirror decryption techniques implemented by the medication dispenser—to encrypt an authentication key and a prescription parameters for the cartridge, write the encrypted authentication key and prescription parameters to the cartridge, and then ship the cartridge to the patient. In this variation, when the medication dispenser is assigned and distributed to the patient, the pharmacy can program the medication dispenser with an assigned decryption key and associate this decryption key with the patient's ID, such as in the patient's medication record. Thus, the medication dispenser can apply a unique decryption scheme stored locally to an encrypted authentication key and prescription parameters read from a cartridge installed therein to locally authorize use of the cartridge with the medication dispenser. Additionally or alternatively, the pharmacy can include a checksum or a digital signature computed from the assigned data fields to verify cartridge authenticity and protect against modification by an unauthorized party. Similarly, the pharmacy can encode the cartridge ID using a one-time password scheme to further increase security.

In this variation, because authentication keys and prescription IDs or prescription parameters are stored locally on each cartridge, the medication dispenser can implement Blocks of the method to confirm or discard use of a cartridge and to access prescription parameters for the cartridge without network connectivity. Furthermore, in this variation of the method, none of the cartridge, the medication dispenser, or the mobile computing device exposes unencrypted patient and prescription information to external systems while functioning with or without an Internet connection.

7. Medication Windows

According to the method, the dispenser assembly, the native medication tracking application, and/or the remote server can track a medication dosage window and a medication dosage interval for consumption of a medication contained in the medication dispenser assembly. In particular, the dispenser assembly and/or the native medication tracking application can implement these prescription parameters to remind the patient when to take her medication and in what dosage. Furthermore, the native medication tracking application can also advise the patient on missed medication dosages (e.g., skipping a day and throwing away the missed reminder pill(s), taking two active pills in a day, advising the patient to obtain an emergency contraceptive and/or pushing a notification to the pharmacy). For example, if the prescription parameters for the cartridge loaded into the medication dispenser require a 24-hour administration interval and a one-hour window but the patient frequently does not adhere to this regimen, the native medication tracking application can dynamically adjust the parameters or their implementation to redress this issue. For example, the native medication tracking application can display additional notifications—through the patient's mobile computing device—showing an altered dosage for the medication in order to maintain overall adherence to the prescription parameters. Additionally or alternatively, the native medication tracking application and/or the dispenser assembly can implement new prescription parameters set by an authorized party, such as the pharmacy or a doctor, after the medication cartridge is supplied to the patient and before the cartridge is emptied. For example, a doctor or pharmacist can modify prescription parameters (e.g., dosage, dosage, medication window duration, limits of daily variations in time of medication consumption, etc.) for the patient specifically, for a subset of patient's prescribed a medication, or for all patient's prescribed a medication, and the remote computer system can write the new or revised prescription parameters to the patient's digital medication record. When the patient's mobile computing device and/or medication dispenser later comes online (i.e., connects to the Internet), the remote computer system can push these new prescription parameters to the mobile computing device or to the medication dispenser, and the native medication tracking application and/or the medication dispenser can implement these new or modified prescription parameters as described herein.

The medication dispenser and the native medication tracking application can collect patient medication consumption data and/or patient feedback and can upload these data to the pharmacy, and the pharmacy can adjust the medication interval and window based on historical patient behavior and feedback for the medication, such as in a subsequent medication cartridge for the same medication. The native medication tracking application can also automatically push notifications to the remote computer system (e.g., to the pharmacy) if a replacement medication cartridge is required for the patient. For example, when the cartridge nears completion (e.g., one day before the shipping time window length), the dispenser assembly pushes a prescription refill notification to the remote computer system, and the remote computer system pushes this notification to the pharmacy where a new cartridge is labeled with the same prescription information and a new cartridge ID, and the new cartridge is shipped to the patient in time to continue the prescription without interruption.

Prior to complete parameter overrun, the remote computer system can push notifications to the dispenser assembly and/or to the mobile computing device to warn of impending cartridge invalidation. If one or more of these parameters is exceeded, the dispenser assembly can invalidate the cartridge ID and push a notification to the remote computer system to create a new cartridge to replace the current cartridge. If the remote computer system, the medication dispenser, and/or the native medication tracking application is/are unable to authenticate the cartridge, the dispenser assembly can still dispense pills from the cartridge, but features such as dosage window notifications and medication consumption prompts can be disabled by the medication dispenser. The dispenser assembly and/or the native medication tracking application can also push notifications to the pharmacy indicating that an unauthorized cartridge is in use with a medication dispenser associated with a patient ID.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for providing treatment of a medical condition with a hardware medication dispenser configured to track medication consumption adherence, the method comprising:
    obtaining, by the hardware medication dispenser, a first unique medication cartridge identifier from a first medication cartridge installed in the hardware medication dispenser, wherein the first medication cartridge includes medication;
    obtaining, by the hardware medication dispenser or a mobile device, a set of unique medication cartridge identifiers assigned to the hardware medication dispenser and associated with a patient medication record, wherein each respective unique medication cartridge identifier of the set of unique medication cartridge identifiers is associated with a respective medication cartridge authorized for use with the hardware medication dispenser;
    determining, by the hardware medication dispenser, the mobile device, or a remote computing system, a first determination that the first unique medication cartridge identifier matches one unique medication cartridge identifier among the obtained set of unique medication cartridge identifiers or a second determination that the first unique medication cartridge identifier does not match one unique medication cartridge identifier among the obtained set of unique medication cartridge identifiers;
    authenticating, by the hardware medication dispenser, the mobile device, or the remote computing system, use of the first medication cartridge with the hardware medication dispenser based on the first determination; and
    disabling, by the hardware medication dispenser, a feature of the hardware medication dispenser based on the second determination while still allowing the medication to be dispensed from the first medication cartridge with the hardware medication dispenser.

2. The method of claim 1, further comprising:
    providing, by the hardware medication dispenser or the mobile device, notifications related to the medication upon authentication.

3. The method of claim 2, wherein the notifications include visual notifications, audible notifications, or haptic notifications.

4. The method of claim 1, wherein the feature includes providing, by the hardware medication dispenser or the mobile device, notifications related to the medication.

5. The method of claim 1, wherein the feature includes medication window tracking.

6. The method of claim 1, wherein the feature includes medication consumption prompts.

7. The method of claim 1, wherein the feature includes push notifications related to the medication.

8. The method of claim 1, wherein the feature includes medication storage sensor tracking.

9. The method of claim 1, wherein the feature includes tracking when medication is removed from the medication dispenser.

10. The method of claim 1, wherein the medication includes pills and the first medication cartridge includes one or more wells configured to house individual pills.

11. The method of claim 1, further comprising:
    causing, by the hardware medication dispenser or the mobile device, custom medication parameters associated with the first unique medication cartridge identifier to be retrieved from a prescription database, wherein the custom medication parameters specify a custom dose of the medication to be consumed during a custom medication time window.

12. The method of claim 1, wherein the first medication cartridge includes generic medication parameters encoded thereon.

13. The method of claim 1, further comprising:
    obtaining, by the medication dispenser, sensor data indicative of the presence or absence of medication in the first medication cartridge; and
    causing, by the medication dispenser, a refill notification to be transmitted to a pharmacy based on the sensor data.

14. The method of claim 13, wherein the sensor data indicative of the presence or absence of medication in the first medication cartridge includes information on how much medication remains in the first medication cartridge.

15. A system configured to provide treatment of a medical condition and track medication consumption adherence, the system comprising:
- a first medication cartridge comprising a first unique medication cartridge identifier, wherein the first unique medication cartridge identifier includes medication; and
- a medication device comprising a cavity configured to receive the first medication cartridge, wherein the medication device is configured to:
  - obtain the first unique medication cartridge identifier from the first medication cartridge;
  - obtain a set of unique medication cartridge identifiers assigned to the medication device and associated with a patient medication record, wherein each respective unique medication cartridge identifier of the set of unique medication cartridge identifiers is associated with a respective medication cartridge authorized for use with the medication device;
  - determine a first determination that the first unique medication cartridge identifier matches one unique medication cartridge identifier among the set of unique medication cartridge identifiers or a second determination that the first unique medication cartridge identifier does not match one unique medication cartridge identifier among the set of unique medication cartridge identifiers;
  - authenticate use of the first medication cartridge with the medication device based on the first determination; and
  - disable a feature of the medication device based on the second determination while still allowing the medication to be dispensed from the first medication cartridge with the medication device.

16. The system of claim 15, wherein the medication device comprises a wireless transmitter configured to transmit a notification to a mobile computing device upon detecting removal of medication from the first medication cartridge.

17. A device for patient-specific secured medication dispensing, the device comprising:
- a cavity configured to receive a medication cartridge comprising a programmable chip with an encrypted cartridge identifier and a patient identifier including medication parameters written onto the programmable chip;
- a memory configured to store a decryption key for decrypting the cartridge identifier;
- a first processor confirming use of the cartridge upon inserting the cartridge into the cavity by:
  - decrypting the cartridge identifier with the decryption key; and
  - verifying the patient identifier accessed using the decrypted cartridge identifier corresponds to a patient associated with the device;
- a second processor determining a medication dose based on the medication parameters obtained from the cartridge; and
- a display presenting a visual indication of the medication dose to be consumed by the patient;
- wherein a hash algorithm is used to encrypt the cartridge identifier.

18. The device of claim 17 wherein the cartridge comprises one or more wells configured to house individual pills.

19. The device of claim 18, wherein each of the one or more wells comprises a sensor configured to generate sensor data specifying a number of pills remaining within the cartridge.

20. The device of claim 19, further comprising a third processor generating a notification upon determining, based on the sensor data, that the number of individual pills remaining in the cartridge is less than the medication dose.

21. The device of claim 20, further comprising a wireless transmitter configured to transmit the refill notification to a mobile device associated with the patient.

22. The device of claim 21, wherein the refill notification is transmitted to a pharmacy.

23. The device of claim 17, wherein the first processors blocks the use of the cartridge by failing to decrypt the cartridge identifier using the decryption key upon inserting the cartridge into the cavity.

* * * * *